(12) United States Patent
Huang

(10) Patent No.: US 8,049,010 B2
(45) Date of Patent: Nov. 1, 2011

(54) SYNTHETIC METHOD AND INTERMEDIATES OF ROSUVASTATIN CALCIUM AND PREPARATION METHODS OF INTERMEDIATES

(75) Inventor: Qingyun Huang, Hefei (CN)

(73) Assignee: Anhui Qingyun Pharmaceuticals & Chemical Co., Ltd., Anhui (CN)

( * ) Notice: Subject to any disclaimer, the term of this patent is extended or adjusted under 35 U.S.C. 154(b) by 1065 days.

(21) Appl. No.: 11/795,123

(22) PCT Filed: Nov. 18, 2005

(86) PCT No.: PCT/CN2005/001958
§ 371 (c)(1),
(2), (4) Date: Jul. 11, 2007

(87) PCT Pub. No.: WO2006/076845
PCT Pub. Date: Jul. 27, 2006

(65) Prior Publication Data
US 2008/0091014 A1      Apr. 17, 2008

(30) Foreign Application Priority Data
Jan. 19, 2005    (CN) .......................... 2005 1 0038203

(51) Int. Cl.
*C07D 239/42*   (2006.01)
*C07D 405/06*   (2006.01)
*C07D 403/12*   (2006.01)
*C07D 413/12*   (2006.01)

(52) U.S. Cl. ......................... 544/297; 544/249; 544/332

(58) Field of Classification Search .................. 544/297, 544/249
See application file for complete search history.

(56) References Cited

U.S. PATENT DOCUMENTS 5,260,440 A * 11/1993 Hirai et al. .................... 544/332
2009/0124803 A1 * 5/2009 Deshpande ................. 544/322

FOREIGN PATENT DOCUMENTS

| WO | WO 0049014 A1 | * | 8/2000 |
| WO | WO 03009714 A2 | * | 11/2003 |
| WO | WO 2004103977 A2 | * | 12/2004 |
| WO | WO 2005063728 A2 | * | 7/2005 |

* cited by examiner

*Primary Examiner* — Venkataraman Balasubramanian
(74) *Attorney, Agent, or Firm* — Antonio Papageorgiou; Ostrow Kaufman LLP

(57) ABSTRACT

The present invention publicly discloses a synthetic method and intermediates of rosuvastatin calcium and synthetic methods of the intermediates. The synthetic method uses 4-4'-fluorophenyl-6-isopropyl-2-(N-methyl-N-methylsulfonylamino)pyridine-5-formaldehyde as the raw material, includes 4-4'-fluorophenyl-6-isopropyl-2-(N-methyl-N-methylsulfonylamino)pyridine-5-acrylonitrile (intermediate I) from a nitrilized reaction, and 4-4'-fluorophenyl-6-isopropyl-2-(N-methyl-N-methylsulfonylamino)pyridine-5-acraldehyde (intermediate II) from an aldehydized reaction of the intermediate I, and further goes through such unit processes as side-chain extension, ketone-group reduction, ethyl-group hydrolysis and neutralization reaction or decomposition reaction to obtain rosuvastatin calcium. The nitrilized reagent can be phosphate diethylacetonitrile, acetonitrile, etc.; the aldehyde reductant can be diisobutyl aluminum hydride, red aluminum, etc.; and the ketone-group reductant can be diethylmethoxyborane, $NaBH_4$, $KBH_4$, etc.

10 Claims, No Drawings

SYNTHETIC METHOD AND INTERMEDIATES OF ROSUVASTATIN CALCIUM AND PREPARATION METHODS OF INTERMEDIATES

CROSS-REFERENCE TO RELATED PATENT APPLICATIONS

The present application claims priority to PCT application PCT/CN2005/001958, filed Nov. 18, 2005, which claims priority to Chinese Patent Application No. 200510038203.0, filed Jan. 19, 2005, which are herein incorporated in their entirety.

FIELD OF THE INVENTION

The present invention relates to a preparation method of a known drug compound, specially relates to a preparation method of a statin-type drug compound, and to speak specifically, relates to a synthetic method and intermediates of rosuvastatin calcium as an antihyperlipidemic drug.

BACKGROUND OF THE INVENTION

Rosuvastatin calcium is a clinical antihyperlipidemic drug, with a chemical name being (+)-(3R,5S)-7-[4-(4-fluorophenyl)-6-isopropyl-2-(N-methyl-N-methylsulfonylamino)pyrimidine-5-yl]-3,5-Dihydroxy-6(E)-calcium heptenoate (2:1), and a chemical structural formula as below:

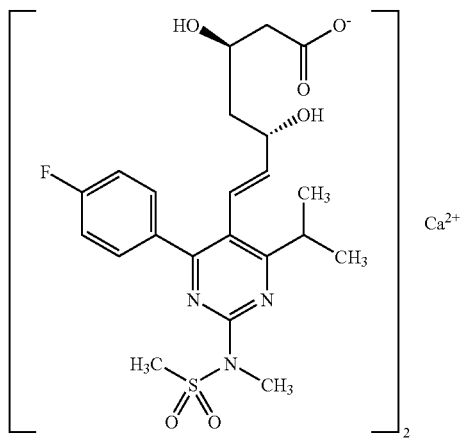

Three preparation methods were reported in the literature as follows:
3. Publicly disclosed in CN1340052A

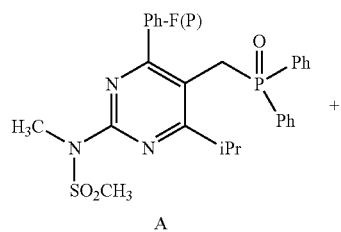

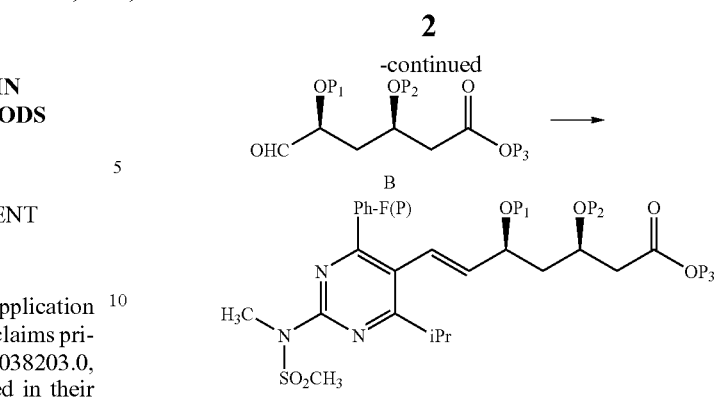

where P1 and P2 are protecting groups of hydroxy, and P3 is a tert-butyl group.

At the presence of a strong base, let an oxidized diphenyl [4-(4-fluorophenyl)-6-isopropyl-2-[methyl(methylsulfonylamino)amino]pyrimidine-5-ylmethyl]phosphine react with 2-[(4R,6S)-6-formyl group-2,2-dimethyl-1,3-dioxa-4-yl] tert-butyl acetate, then disconnect the protecting group of dihydroxy in the product, alkalinely hydrolyze the tert-butyl ester group, and finally produce rosuvastatin calcium as a calcium salt.

In the first route, it takes a long reaction time to synthesize a phosphine (A), with a low yield and at the same time a usage of highly toxic and severely pollutive $PBr_3$. There are many synthetic methods of its side chain (B) (U.S. Pat. No. 5,278,313, EP0319847, U.S. Pat. No. 5,399,722, U.S. Pat. No. 5,481,009, U.S. Pat. No. 5,998,633, U.S. Pat. No. 6,140,527, EP0104750, and WO0307733), but most of them have such problems as a long synthetic route (7-9 steps), most of intermediates being viscous, multiple steps of high vacuum (around 0.1 mmHg) distillation and silica gel column purification, a usage of hypertoxic potassium cyanide or sodium cyanide, a poor purity of products, unsteadiness, and difficulty in production industrialization.

4.

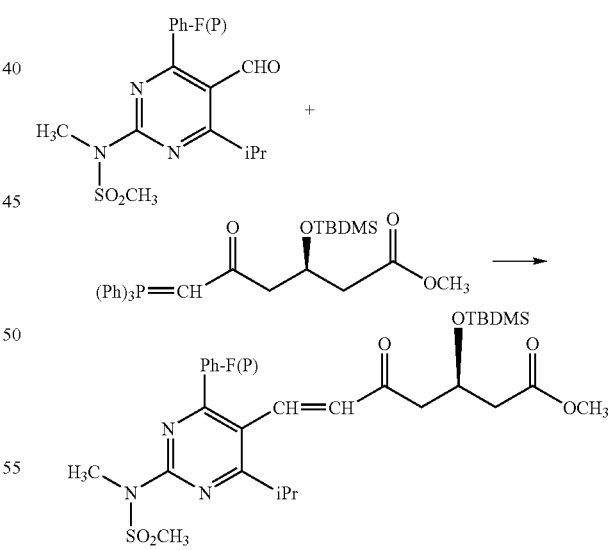

TBDMS is a protecting group of tert-butyl dimethyl silane.

The second route is difficult in synthesizing the side chain (D) (JP5-32680 and J. Org. Chem., 1994, 59 (25). 7849-7854), with a long route, intermediates of each step being mostly viscous, difficulty in separation and purification (need to go through multiple steps of silica gel column purification), a poor purity of products, and unsteadiness. The yield of connection of the side chain (D) to the main ring (C) is low, with a poor purity of products.

3. Publicly disclosed in WO2004/052867

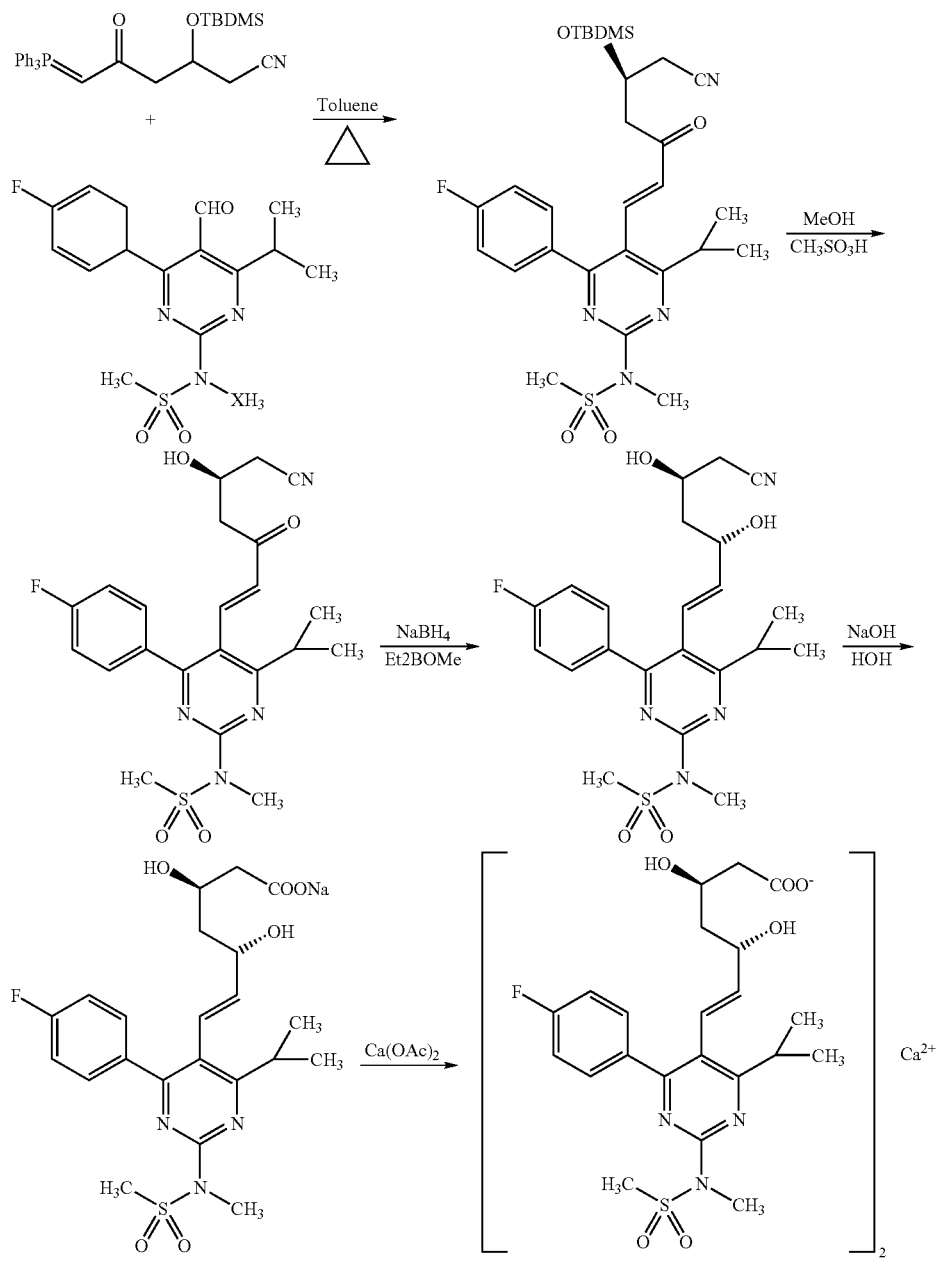

In the third route, there is no synthetic method of the side chain (E), the yield of connection of the side chain to the main ring (C) is low, and multiple steps of silica gel column purification are required, with no physical constants for each intermediate, no detection methods for product purity or reaction progress, only testing results for small quantities, and no amplified data.

SUMMARY OF THE INVENTION

Preparation methods of drug compounds are different with different starting materials on one hand, and can obtain the same target products from the same starting materials by taking different process routes on the other, namely the so-called all roads lead to Rome. The present invention is just developed according to this approach.

The present invention also use 4-4'-fluorophenyl-6-isopropyl-2-(N-methyl-N-methylsulfonylamino)pyrimidine-5-formaldehyde (hereinafter referred to as the "substitution pyrimidine-5-formaldehyde") as the starting material (this starting material is the same as that in the $2^{nd}$ and $3^{rd}$ methods in BACKGROUND OF THE INVENTION), but takes the following process route to synthesize rosuvastatin calcium (hereinafter referred to as the "target product").

3. First, prepare a new intermediate I using the starting material and a nitrilized reagent Produce 4-4'-fluorophenyl-6-isopropyl-2-(N-methyl-N-methylsulfonylamino)pyrimidine-5-acrylonitrile, i.e. the intermediate I (hereinafter referred to as the "substitution pyrimidine-5-acrylonitrile"), by condensation of the substitution pyrimidine-5-formaldehyde with the nitrilized reagent.

The nitrilized reagent can be phosphate diethylacetonitrile, acetonitrile, etc. A molar ratio of the substitution pyrimidine-5-formaldehyde to the nitrilized reagent is 1.0:0.5-10.0, preferably 1.0:0.8-2.0.

If phosphate diethylacetonitrile is used, add it into an organic solvent together with the starting material, and titrate with a NaOH solution of 15-25% by weight at room temperature until the reaction solution is pink and clear, add a certain amount of catalyst Aliquat336 (methyl trioctyl ammonium chloride), continue to react at room temperature for 2-4 hours, and with the product precipitating obtain the substitution pyrimidine-5-acrylonitrile (the intermediate I) after separation and purification.

The organic solvent can be benzene, toluene, xylene, etc.

4. Reduce the acrylonitrile group to the acrolein group, and obtain a new intermediate II The substitution pyrimidine-5-acrylonitrile (the intermediate I) reacts with a reductant to produce 4-4'-fluorophenyl-6-isopropyl-2-(N-methyl-N-methylsulfonylamino) pyrimidine-5-acraldehyde, i.e. the intermediate II (hereinafter referred to as the "substitution pyrimidine-5-acraldehyde").

The reductant can be diisobutyl aluminum hydride, red aluminum, etc. If diisobutyl aluminum hydride is selected, titrate the substitution pyrimidine-5-acrylonitrile (the intermediate I) in an organic solvent with 10-55% toluene solution of diisobutyl aluminum hydride under the protection of an inert gas at −15~−5° C., continue to react after the titration for 1-2 hours, and obtain the substitution pyrimidine-5-acraldehyde after the reaction through separation and purification.

The organic solvent can be benzene, toluene, xylene, etc.

A molar ratio of the substitution pyrimidine-5-acrylonitrile to diisobutyl aluminum hydride is 1.0:0.5-10.0, preferably 1.0:0.8-4.0.

3. Condensate acraldehyde and extend the chain thereof to obtain an intermediate III Dissolve the substitution pyrimidine-5-acraldehyde (the intermediate III) in tetrahydrofuran and protect with the inert gas, agitate it to uniformity at the presence of S-dinaphthol, isopropyl titanate, lithium chloride and tetramethyl ethylene diamine, add 1,3-bis(trimethyl siloxane)-1-ethoxy-1,3-butadiene and react at 20-35° C. for 2-4 hours, remove the protecting group through acidolysis after the reaction, and separate and purify to obtain the intermediate III, i.e. 7-[4-4'-fluorophenyl-6-isopropyl-2-(N-methyl-N-methylsulfonylamino)pyrimidine-5-yl]-3-oxo-(5R)-5-hydroxy-(E)-6-ethyl heptenoate (hereinafter referred to as the "substitution pyrimidine-5-ketone and hydroxy ethyl heptenoate").

A molar ratio of the substitution pyrimidine-5-acraldehyde to 1,3-bis(trimethyl siloxane)-1-ethoxy-1,3-butadiene is 1.0:0.5-10.0, preferably 1.0:1.0-5.0. 1,3-bis(trimethyl siloxane)-1-ethoxy-1,3-butadiene can be prepared according to methods in the relevant literature.

S-dinaphthol, isopropyl titanate, lithium chloride and tetramethyl ethylene diamine are all catalysts, which can increase not only reaction rate but also reaction stereoselectivity. The usage of them is 1-20% (molar ratio) of the substitution pyrimidine-5-acraldehyde, preferably 5-10%.

The molar ratio of S-dinaphthol to isopropyl titanate is 1:0.5-4, preferably 1:0.8-2.

4. Reduce ketone and hydroxy ethyl heptenoate to dihydroxy ethyl heptenoate to obtain an intermediate IV Use a reductant to reduce the ketone group on the side chain of the substitution pyrimidine-5-ketone and hydroxy ethyl heptenoate (the intermediate III) to a hydroxyl group, and obtain the intermediate IV, i.e. 7-[4-4'-fluorophenyl-6-isopropyl-2-(N-methyl-N-methylsulfonylamino)pyrimidine-5-yl]-(3R,5S)-dihydroxy-(E)-6-ethyl heptenoate (hereinafter referred to as the "substitution pyrimidine-5-dihydroxy ethyl heptenoate").

The reductant can be $NaBH_4$, $KBH_4$ and diethylmethoxyborane, etc.

5. Obtain the target product from the intermediate IV through a known chemical process, i.e. firstly hydrolyze the carbethoxy group; if an acid is used, a corresponding carboxylic acid is obtained; and if a base is used, a corresponding carboxylate is obtained. The former can react with $Ca(OH)_2$ through a neutralization reaction to produce the target product, while the latter can react with a dissoluble inorganic/organic acid salt of calcium to produce the target product through a double decomposition reaction.

The ketone group reduction and the side-chain extension of the present invention reference methods in the prior technical literature.

Physico-chemical data of the target product are as below: White powder or crystalline powder, odorless, and bitter taste; easily soluble in chloroform, soluble in acetone, slightly soluble in methyl alcohol, and slightly soluble in water; and the specific rotation is +14° to +20° (1% and 50% methyl alcohol).

This synthetic method is short in route, and high in yield; intermediates of each step are mostly solid and easy to purify, and therefore purity of the product is high; meanwhile, neither highly toxic raw materials nor high vacuum distillation or chromatography methods are needed, and therefore it is easy to be industrialized. Application of the present invention can greatly shorten a production cycle, reduce production costs, and abate the "three wastes".

DETAILED DESCRIPTION OF THE EMBODIMENTS

Here for instance, use phosphate diethylacetonitrile as the nitrilized reagent, and diisobutyl aluminum hydride and $NaBH_4$ as the reductant. Embodiments, but not limited to, are described as follows:

Embodiment 1

(1) Synthesis of 4-4'-fluorophenyl-6-isopropyl-2-(N-methyl-N-methylsulfonylamino)pyrimidine-5-acrylonitrile Add 30 g of 4-4'-fluorophenyl-6-isopropyl-2-(N-methyl-N-methylsulfonylamino) pyrimidine-5-formaldehyde into a reaction flask of 500 ml, add toluene 130 ml, and start to agitate. Add in turn phosphate diethylacetonitrile 20.5 g and Aliquat336 (catalyst) 1.4 g, and titrate with 20% sodium hydroxide solution 62.7 g below 25° C., with the reaction solution gradually clarifying and turning out to be a pink clear solution after titration. React for 3 hours at room temperature, and a white solid precipitates. Filter with a pump, wash with water, pump, and dry, and obtain a white solid 30.5 g with a yield of 95.4%.

(2) Synthesis of 4-4'-fluorophenyl-6-isopropyl-2-(N-methyl-N-methylsulfonylamino)pyrimidine-5-acraldehyde Add 30 g of 4-4'-fluorophenyl-6-isopropyl-2-(N-methyl-N-methylsulfonylamino)pyrimidine-5-acrylonitrile into a four-opening reaction flask of 500 ml aerated with a protective nitrogen gas, add anhydrous toluene 280 ml, agitate, cool in an ice-salt bath to below −10° C., titrate with 40% toluene solution of diisobutyl aluminum hydride 38 ml, react for an hour after the titration, and titrate with absolute alcohol 16 ml first. Add diluted hydrochloric acid to process, separate the liquids, add 1 M hydrochloric acid 200 ml to wash the oil layer once, wash with saturated NaHCO$_3$ to neutral, dry with anhydrous Na$_2$SO$_4$, evaporate the solvent by revolving, crystallize remains with hexane-petroleum ether, and obtain a white solid 26.3 g, mp. 92-94° C., with a yield of 87%.

(3) Synthesis of 4-4'-fluorophenyl-6-isopropyl-2-(N-methyl-N-methylsulfonylamino)pyrimidine-5-yl-3-oxo-(5R)-5-hydroxy-(E)-6-ethyl heptenoate Add 25 g of 4-4'-fluorophenyl-6-isopropyl-2-(N-methyl-N-methylsulfonylamino)pyrimidine-5-acraldehyde into a four-opening reaction flask of 500 ml aerated with a protective nitrogen gas, add tetrahydrofuran 335 g to dissolve, add a toluene solution of S-dinaphthol and titanate isopropyl acid (molar ratio 1:1) 8.35 g, add lithium chloride 1.5 g and tetramethyl ethylene diamine 8.14 g, and after agitating to uniformity add 1,3-bis(trimethyl siloxane)-1-ethoxy-1,3-butadiene 31.34 g. Agitate the mixture for 3 hours at 20-30° C., add 50% H$_2$SO$_4$ 21.9 g at 0° C. after the reaction, filter after 2 hours, add ethyl acetate into the filtrate, wash the oil layer with water and saturated brine, and dry with anhydrous Na$_2$SO$_4$; evaporate the solvent under a reduced pressure, crystallize remains with hexane-petroleum ether, and obtain a solid 28.2 g, with a yield of 83.9%.

(4) Synthesis of 7-[4-4'-fluorophenyl-6-isopropyl-2-(N-methyl-N-methylsulfonylamino)pyrimidine-5-yl]-(3R,5S)-dihydroxy-(E)-6-ethyl heptenoate Dissolve 13 g of 7-[4-4'-fluorophenyl-6-isopropyl-2-(N-methyl-N-methylsulfonylamino)pyrimidine-5-yl]-3-oxo-(5R)-5-hydroxy-(E)-6-ethyl heptenoate into anhydrous tetrahydrofuran 350 ml and methyl alcohol 90 ml, and titrate with 1 M tetrahydrofuran solution of diethylmethoxyborane 31.7 ml at −78° C. Agitate the mixture for 30 minutes at −78° C., add NaBH$_4$ 1.3 g, and agitate for 3 hours at −78° C. Add glacial acetic acid 16 ml after the reaction, neutralize with NaHCO$_3$, extract with ether, wash the organic layer with water, dry, and obtain the product 11.4 g, mp. 92-94° C., with a yield of 85%.

(5) Synthesis of 7-[4-4'-fluorophenyl-6-isopropyl-2-(N-methyl-N-methylsulfonylamino)pyrimidine-5-yl]-(3R,5S)-dihydroxy-(E)-6-calcium heptenoate Add 11.4 g of 7-[4-4'-fluorophenyl-6-isopropyl-2-(N-methyl-N-methylsulfonylamino)pyrimidine-5-yl]-(3R,5S)-dihydroxy-(E)-6-ethyl heptenoate into a reaction flask of 500 ml, agitate and titrate with 1 N sodium hydroxide solution 22.3 ml in an ice-water bath, react for an hour in the ice-water bath, titrate with a solution of CaCl$_2$ 1.3 g dissolved in water 180 ml, with the reaction solution gradually becoming turbid and a white solid precipitating, continue to agitate overnight after the titration, filter with a pump, wash with water, dry, and obtain a white product 10.8 g, with a yield of 96% and an optical purity of ee>99%.

Embodiment 2

(1) Synthesis of 4-4'-fluorophenyl-6-isopropyl-2-(N-methyl-N-methylsulfonylamino)pyrimidine-5-acrylonitrile Add 30 g of 4-4'-fluorophenyl-6-isopropyl-2-(N-methyl-N-methylsulfonylamino)pyrimidine-5-formaldehyde into a reaction flask of 500 ml, add toluene 140 ml, and start to agitate. Add in turn phosphate diethylacetonitrile 16.4 g and Aliquat336 1.6 g, and titrate with 20% sodium hydroxide solution 60.5 g below 25° C., with the reaction solution gradually clarifing and turning out to be a pink clear solution. React for 4 hours at room temperature, and a white solid precipitates. Filter with a pump, wash with water, drain with a pump, dry, and obtain a white solid 28.5 g, with a yield of 89.1%.

(2) Synthesis of 4-4'-fluorophenyl-6-isopropyl-2-(N-methyl-N-methylsulfonylamino)pyrimidine-5-acraldehyde Add 60 g of 4-4'-fluorophenyl-6-isopropyl-2-(N-methyl-N-methylsulfonylamino)pyrimidine-5-acrylonitrile into a four-opening reaction flask of 100 ml aerated with a protective nitrogen gas, add anhydrous toluene 5,000 ml, agitate, cool in an ice-salt bath to below −15° C., titrate with 35% toluene solution of diisobutyl aluminum hydride 70 ml, react for 2 hours after the titration, and titrate with absolute alcohol 30 ml first. Add diluted hydrochloric acid to process, separate the liquids, add 1 M hydrochloric acid 360 ml to wash the oil layer once, wash with saturated NaHCO$_3$ to neutral, dry with anhydrous Na$_2$SO$_4$, evaporate the solvent by revolving, crystallize remains with hexane-petroleum ether, and obtain a white solid 50.3 g, mp. 91-93° C., with a yield of 83.2%.

(3) Synthesis of 4-4'-fluorophenyl-6-isopropyl-2-(N-methyl-N-methylsulfonylamino)pyrimidine-5-yl]-3-oxo-(5R)-5-hydroxy-(E)-6-ethyl heptenoate Add 25 g of 4-4'-fluorophenyl-6-isopropyl-2-(N-methyl-N-methylsulfonylamino)pyrimidine-5-acraldehyde into a four-opening reaction flask of 500 ml aerated with a protective nitrogen gas, add tetrahydrofuran 400 ml to dissolve, and add a tetrahydrofuran solution of S-dinaphthol and titanate isopropyl acid (molar ratio 1:1) 5.25 g. Add lithium chloride 1.0 g and tetramethyl ethylene diamine 8.5 g, and after agitating to uniformity add 1,3-bis(trimethyl siloxane)-1-ethoxy-1,3-butadiene 25.14 g. Agitate the mixture for 3 hours at 18-25° C., add 10% HF 23.9 g at 0° C. after the reaction, filter after 2 hours, add ethyl acetate into the filtrate, wash the oil layer with water and saturated brine, and dry with anhydrous Na$_2$SO$_4$; evaporate the solvent under a reduced pressure, crystallize remains with hexane-petroleum ether, and obtain a solid 26.2 g, with a yield of 77.9%.

Embodiment 3

Based on the solution of embodiment 1, an alternative solution for proportion and reactant selection as below can be used, with the rest the same as embodiment 1.

30 g of 4-4'-fluorophenyl-6-isopropyl-2-(N-methyl-N-methylsulfonylamino)pyrimidine-5-formaldehyde.

The nitrilized reagent can be phosphate diethylacetonitrile, acetonitrile, etc. A molar ratio of the substitution pyrimidine-5-formaldehyde to the nitrilized reagent is 1.0:0.5-10.0, preferably 1.0:0.8-2.0.

The aldehydized reductant can be diisobutyl aluminum hydride, red aluminum, etc. A molar ratio of the substitution pyrimidine-5-acrylonitrile to diisobutyl aluminum hydride is 1.0:0.5-10.0, preferably 1.0:0.8-4.0.

The organic solvent can be benzene, toluene, xylene, etc.

S-dinaphthol, isopropyl titanate, lithium chloride and tetramethyl ethylene diamine are all catalysts. The usage of them is 1-20% (molar ratio) of that of the substitution pyrimidine-5-acraldehyde, preferably 5-10%.

A molar ratio of the substitution pyrimidine-5-acraldehyde to 1,3-bis(trimethyl siloxane)-1-ethoxy-1,3-butadiene is 1.0:0.5-10.0, preferably 1.0:1.0-5.0.

The organic solvent can be tetrahydrofuran, toluene, etc.

The scope of each parameter in this embodiment means any parameter within the scope can be used, however, due to text size limitation, it is not planned to enumerate for each parameter.

The invention claimed is:

1. A method for synthesizing an intermediate of rosuvastatin calcium, using 4-4'-fluorophenyl-6-isopropyl-2-(N-methyl-N-methylsulfonylamino)pyrimidine-5-formaldehyde as raw material, comprising:
   a) reacting the raw material with a nitrilized reagent in an organic solvent to produce an intermediate I, 4-4'-fluorophenyl-6-isopropyl-2-(N-methyl-N-methylsulfonylamino)pyrimidine-5-acrylonitrile;
   b) reacting the intermediate I with a reductant to produce an intermediate II, 4-4'-fluorophenyl-6-isopropyl-2-(N-methyl-N-methylsulfonylamino)pyrimidine-5-acraldehyde;
   c) reacting the intermediate II with 1,3-bis(trimethyl siloxane)-1-ethoxy-1,3-butadiene to produce an intermediate III, 7-[4-4'-fluorophenyl-6-isopropyl-2-(N-methyl-N-methylsulfonylamino)pyrimidine-5-yl]-3-oxo-(5R)-5-hydroxy-(E)-6-ethyl heptenoate, wherein the reaction comprises: dissolving the intermediate II in tetrahydrofuran, protecting the intermediate II with an inert gas; adding dinaphthol, isopropyl titanate, and tetramethyl ethylene diamine as catalysts; adding 1,3-bis(trimethyl siloxane)-1-ethoxy-1,3-butadiene after agitating to uniformity, and reacting for 2-4 hours at 20-35° C.; and
   d) reacting the intermediate III with an reductant to produce an intermediate IV, 7-[4-4'-fluorophenyl-6-isopropyl-2-(N-methyl-N-methylsulfonylamino)pyrimidine-5-yl]-(3R,5S)-dihydroxy-(E)-6-ethyl heptenoate.

2. The method of claim 1, wherein the nitrilized reagent is phosphate diethylacetonitrile, and wherein the reaction of step a) comprises: adding the reactants into an organic solvent, thereby producing a reaction solution a); titrating the reaction solution a) with a base solution at room temperature until the reaction solution a) becomes a clear pink solution; adding catalyst Aliquat336 (methyl trioctyl ammonium chloride) after the titration; and reacting at room temperature for 2-4 hours, with a molar ratio of 4-4'-fluorophenyl-6-isopropyl-2-(N-methyl-N-methylsulfonylamino)pyrimidine-5-formaldehyde to the nitrilized reagent being 1.0:0.5-10.0;
   the reductant used in step b) is diisobutyl aluminum hydride, and wherein the reaction of step b) comprises: adding the intermediate I into an organic solvent, thereby producing a reaction solution b); titrating the reaction solution b) with 10-55% toluene solution of diisobutyl aluminum hydride under the protection of $N_2$ gas at −15~−5° C.; continue reacting after the titration for 1-2 hours; wherein a molar ratio of 4-4'-fluorophenyl-6-isopropyl-2-(N-methyl-N-methylsulfonylamino) pyrimidine-5-acrylonitrile to diisobutyl aluminum hydride is 1.0:0.5-10.0;
   the reductant used in the step d) is $NaBH_4$, and wherein the reaction of step d) comprises: dissolving the intermediate III in a hybrid solvent of tetrahydrofuran and methyl alcohol, and reacting with $NaBH_4$ for 2-4 hours at the presence of diethylmethoxyborane at −80~−50° C.;
   wherein the reaction of step c) further comprises: removing protecting group through acidolysis after the reaction, and separating and purifying the intermediate III;
   a molar ratio of 4-4'-fluorophenyl-6-isopropyl-2-(N-methyl-N-methylsulfonylamino)pyrimidine-5-acraldehyde to 1,3-bis(trimethyl siloxane)-1-ethoxy-1,3-butadiene is 1.0:0.5-10.0;
   the total molar quantity of S-dinaphthol, isopropyl titanate, lithium chloride, and tetramethyl ethylene diamine is 1-20% of that of 4-4'-fluorophenyl-6-isopropyl-2-(N-methyl-N-methylsulfonylamino)pyrimidine-5-acraldehyde; and
   the molar ratio of S-dinaphthol to isopropyl titanate is 1:0.5-4.

3. The method of claim 1, wherein the inert gas is nitrogen gas, the nitrilized reagent is acetonitrile, the reductant used in step b) is red aluminum, the reductant used in step d) is $KBH_4$, and the organic solvent used in step a) is benzene, toluene, or xylene.

4. The method of claim 2, wherein the molar ratio of 4-4'-fluorophenyl-6-isopropyl-2-(N-methyl-N-methylsulfonylamino)pyrimidine-5-formaldehyde to the nitrilized reagent is 1.0:0.8-2.0, the molar ratio of 4-4'-fluorophenyl-6-isopropyl-2-(N-methyl-N-methylsulfonylamino)pyrimidine-5-acrylonitrile to diisobutyl aluminum hydride is 1.0:0.8-4.0, and the molar ratio of 4-4'-fluorophenyl-6-isopropyl-2-(N-methyl-N-methylsulfonylamino)pyrimidine-5-acraldehyde to 1,3-bis(trimethyl siloxane)-1-ethoxy-1,3-butadiene is 1.0:1.0-5.0; the total molar quantity of S-dinaphthol, isopropyl titanate, lithium chloride, and tetramethyl ethylene diamine is 5-10% of that of 4-4'-fluorophenyl-6-isopropyl-2-(N-methyl-N-methylsulfonylamino)pyrimidine-5-acraldehyde, and the molar ratio of S-dinaphthol to isopropyl titanate is 1:0.8-2.

5. The intermediate used for preparation of rosuvastatin calcium according to claim 1, wherein the intermediate is a compound having the following chemical structural formula:

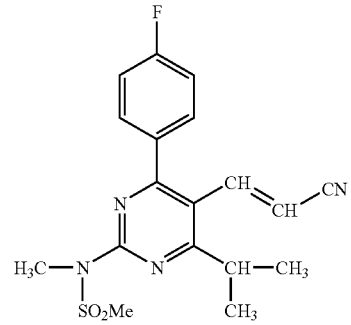

with a chemical name being 4-4'-fluorophenyl-6-isopropyl-2-(N-methyl-N-methylsulfonylamino)pyrimidine-5-acrylonitrile, which is a white solid, with a melting point at 136-140° C.

6. The intermediate used for preparation of rosuvastatin calcium according to claim 1, wherein the intermediate is a compound having the following chemical structural formula:

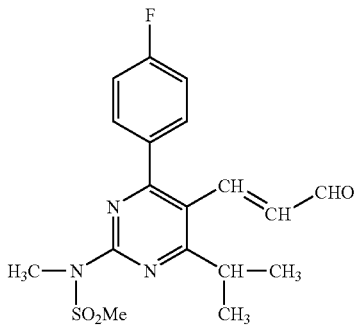

with a chemical name being 4-4'-fluorophenyl-6-isopropyl-2-(N-methyl-N-methylsulfonylamino)pyrimidine-5-acraldehyde, which is a white solid, with a melting point at 90-95° C.

7. A method of preparing the intermediate of claim 5, wherein 4-4'-fluorophenyl-6-isopropyl-2-(N-methyl-N-methylsulfonylamino)pyrimidine-5-formaldehyde reacts with a nitrilized reagent to produce 4-4'-fluorophenyl-6-isopropyl-2-(N-methyl-N-methylsulfonylamino)pyrimidine-5-acrylonitrile.

8. The method of claim 7, wherein the nitrilized reagent is phosphate diethylacetonitrile, where the method comprises: adding the reactants into an organic solvent, thereby producing a reaction solution; titrating the reaction solution with a base solution at room temperature until the reaction solution turns into a clear pink solution; and reacting at room temperature for 2-4 hours after the titration; and wherein the molar ratio of 4-4'-fluorophenyl-6-isopropyl-2-(N-methyl-N-methylsulfonylamino)pyrimidine-5-formaldehyde to the nitrilized reagent is 1.0:0.5-10.0.

9. A method of preparing the intermediate according to claim 6, wherein 4-4'-fluorophenyl-6-isopropyl-2-(N-methyl-N-methylsulfonylamino)pyrimidine-5-acrylonitrile reacts with a reductant to produce 4-4'-fluorophenyl-6-isopropyl-2-(N-methyl-N-methylsulfonylamino) pyrimidine-5-acraldehyde.

10. The method of claim 9, wherein the reductant used is diisobutyl aluminum hydride, where the method comprises: adding the intermediate I into an organic solvent; titrating with 10-55% toluene solution of diisobutyl aluminum hydride under the protection of $N_2$ gas at −15~−5° C.; and continuing to react for 1-2 hours, wherein the molar ratio of 4-4'-fluorophenyl-6-isopropyl-2-(N-methyl-N-methylsulfonylamino)pyrimidine-5-acrylonitrile to diisobutyl aluminum hydride is 1.0:0.5-10.0.

* * * * *